(12) United States Patent
Cull

(10) Patent No.: US 6,875,221 B2
(45) Date of Patent: Apr. 5, 2005

(54) TURBINE DRIVEN VITRECTOMY CUTTER

(75) Inventor: Laurence J. Cull, Wildwood, MO (US)

(73) Assignee: Bausch & Lomb Incorporated, Rochester, NY (US)

(*) Notice: Subject to any disclaimer, the term of this patent is extended or adjusted under 35 U.S.C. 154(b) by 343 days.

(21) Appl. No.: 10/017,561

(22) Filed: Dec. 14, 2001

(65) Prior Publication Data

US 2003/0114870 A1 Jun. 19, 2003

(51) Int. Cl.$^7$ ................................................ A61B 17/32
(52) U.S. Cl. ............................................................ 606/171
(58) Field of Search .................................. 606/171, 170, 606/166; 604/22

(56) References Cited

U.S. PATENT DOCUMENTS

| | | | |
|---|---|---|---|
| 3,584,629 A | * 6/1971 | Hoef et al. | 606/180 |
| 4,108,182 A | * 8/1978 | Hartman et al. | 606/171 |
| 4,246,902 A | * 1/1981 | Martinez | 604/22 |
| 4,314,560 A | * 2/1982 | Helfgott et al. | 606/171 |
| 4,696,298 A | 9/1987 | Higgins et al. | 128/305 |
| 4,827,615 A | * 5/1989 | Graham | 30/166.3 |
| 5,803,733 A | * 9/1998 | Trott et al. | 433/132 |
| 5,893,857 A | * 4/1999 | Shturman et al. | 606/159 |
| 6,258,111 B1 | * 7/2001 | Ross et al. | 606/171 |

* cited by examiner

Primary Examiner—Michael H. Thaler
(74) Attorney, Agent, or Firm—Michael L. Smith

(57) ABSTRACT

A vitreous cutter 10 includes a plurality of vanes 14 rotatably attached within a housing 12. An inlet 16 receives pressurized fluid, which causes rotation of the vanes 14. An outlet 20 allows the pressurized fluid to exit the cutter 10. A cam 24 rotates upon rotation of the vanes 14, which causes reciprocal movement of a vitrectomy probe 28.

2 Claims, 2 Drawing Sheets

TURBINE DRIVEN VITRECTOMY CUTTER

BACKGROUND OF THE INVENTION

1. Field of the Invention

The present invention is directed to high-speed surgical cutters for removing tissue. More particularly, the present invention is related to vitrectomy cutters for use in ophthalmic surgery.

2. Description of the Prior Art

Vitrectomy cutters in ophthalmic surgery are well-known. These cutters typically include a hollow vitrectomy probe, reciprocally contained within an outer sheath. By means of reciprocal movement of the hollow probe, vitreous material is cut by the cooperating action between the outer sheath and the hollow probe. The hollow probe is reciprocated by means of various mechanized movement.

Such movement is accomplished, for example, by electric motor means or by pulsed pressurized air acting on such mechanisms as a diaphragm.

These prior art vitrectomy cutters typically include many moving parts and sealing arrangements.

Therefore, it would be desirable to have a vitrectomy cutter that utilizes fewer parts and is more reliable and less costly to manufacture than previously known.

DETAILED DESCRIPTION OF THE PREFERRED EMBODIMENT

Figure 1:
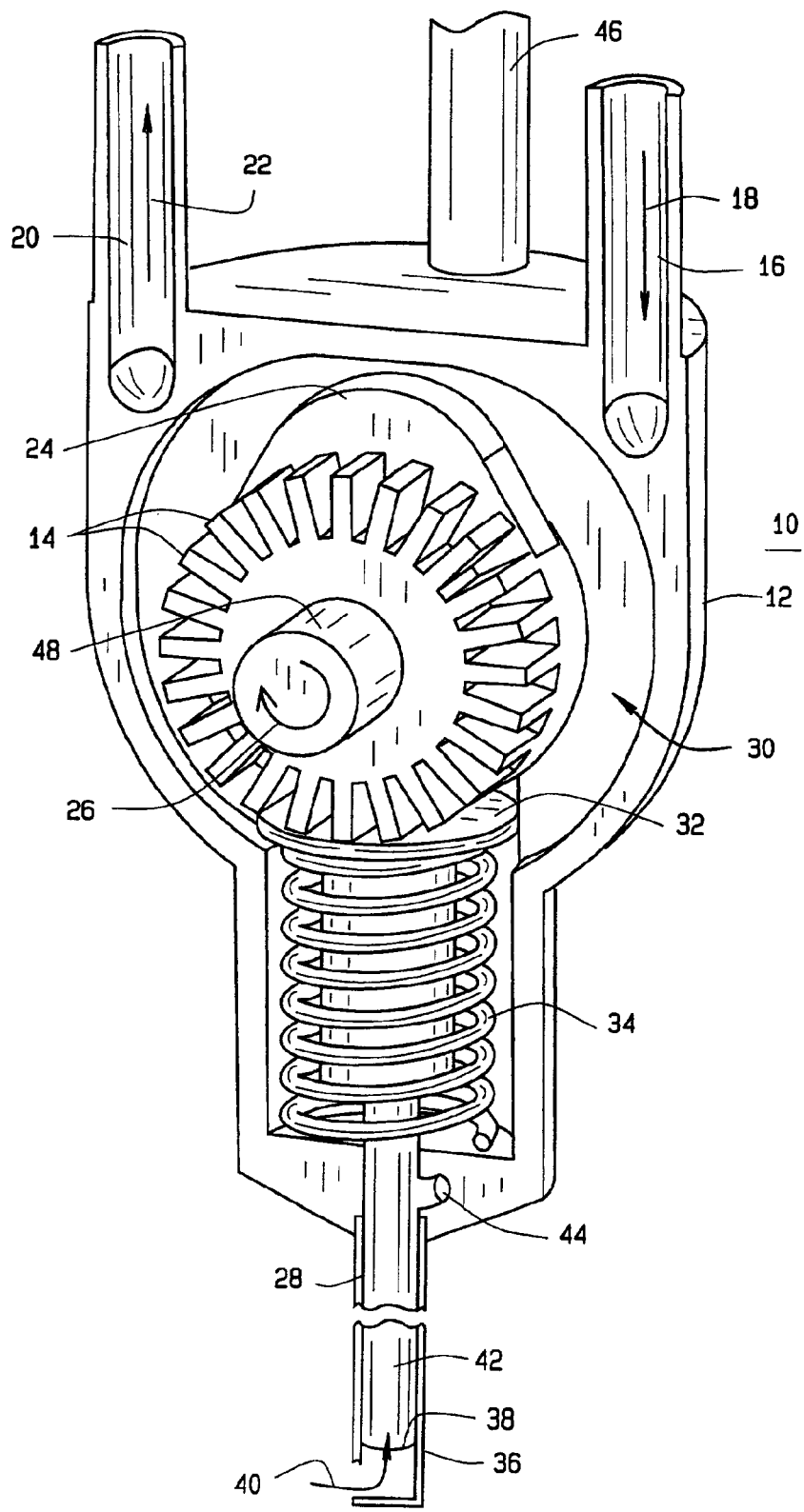
FIG. 1 is a cut-away partial perspective of a vitrectomy cutter in accordance with the present invention.

FIG. 1 shows a cut-away, partial perspective of a vitrectomy or vitreous cutter 10 in accordance with the present invention. Cutter 10 includes a housing 12 and a plurality of vanes 14 which are rotatably attached within the housing. Vanes 14 combine to form a turbine drive. An inlet 16 for receiving pressurized fluids, such as pressurized air, causes rotation of the vanes 14 when air flows, into inlet 16, in the direction of arrow 18. An outlet 20 allows the pressurized fluid to exit the cutter 10 in the direction of arrow 22. A cam 24 is rotatably attached within the housing 12 and structured to rotate upon rotation of the vanes 14. Vanes 14 and cam 24 rotate in the direction of arrow 26 upon the introduction of pressurized fluid into inlet 16 in the direction of arrow 18. Vanes 14 may vary in number, size, and shape from that shown in FIG. 1. The purpose of vanes 14 is to propel the rotation of cam 24 under the influence of a flow of pressurized fluid. A vitrectomy probe 28 contained within the housing 12 is structured for reciprocal movement, caused by the rotation of cam 24, as can be seen in FIG. 1.

Cam 24 may be of various design shapes depending on design requirements. Such requirements include probe extension length, dwell time in both the extended and retracted position, and the travel rate between the extended and retracted positions.

In operation, pressurized fluid, such as pressurized air or other suitable fluid, preferably continuously flows in the direction of arrow 18 into an inner-chamber 30 of housing 12, causing vanes 14 and cam 24 to rotate in the direction of arrow 26. Outlet 20 provides an exit for pressurized fluid to flow out the chamber 30 in the direction of arrow 22. In this way, it is believed that higher cutting rates and higher cutting forces can be achieved than with previous vitrectomy cutters. In addition, a simple arrangement of a continuous air supply may be used with a simple valve (not shown) to turn the air supply on and off. This is opposed to typical prior art pneumatic vitrectomy cutters that require more complicated valving systems to pulse the air supply in order to actuate a diaphragm, which in turn reciprocates a vitrectomy probe. It is believed that cutting rates much higher than rates of prior art cutters can be achieved with the use of the present inventive turbine vitreous cutter.

Vitrectomy probe 28 may further include a cam plate 32 attached to a proximal end of the vitrectomy probe 28. A spring 34 surrounds the vitrectomy probe 28. As can be seen, the spring 34 is positioned between the cam plate 32 and the housing 10, such that the cam plate 32 is biased towards the cam 24. In this way, probe 28 is biased towards a retracted or open position. Rotation of the cam 24 causes reciprocating movement of the vitrectomy probe 28. Vitrectomy probe 28 then cooperates with an outer sheath 36 to cut tissue with tip 38 in a manner well known. Tissue and fluid is preferably aspirated in the direction of arrow 40 through bore 42 of the vitrectomy probe 28. The tissue and fluid is then aspirated from the bore 42 into aspiration channel 44 and out aspiration outlet 46 to a collection reservoir (not shown).

Using a constant or continuous air supply leads to many advantages over the prior art. Prior cutters' need for "pulsed" air led to excessive valve wear and failure compared to the present invention. This is because the present invention may use a simple valve that varies the volume of pressurized fluid from 0 to maximum capacity (this can be controlled by known surgical foot controllers); as compared to prior art valving systems that had to rapidly and repeatedly "pulse" air. The reciprocating action of the probe 28 does not depend on air supply pressure changes, as the prior art does. The speed of vitreous cutter 10 is then not dependent on the response time of a prior art "pulsing" control valve or the need to wait, as in the prior art, for the cutter to vent the pressure during the return stroke.

Similarly cutter 10 is not limited by the response of the prior art's use of diaphragms. The use of diaphragms relies on changes in fluid/air pressure to effect reciprocation of a probe. These pressure changes slow down the speed of cutting compared to cutter 10. Prior art technology has achieved higher cutting speeds by employing thinner diaphragms, which in turn has led to less stiff and less reliable diaphragms.

Compared to prior art pneumatic cutters, cutter 10, through use of cam 24, provides a much greater actuation force. This is because the area in which air pressure acts is greater because of the several vanes 14 versus to single diaphragm of the prior art. Because of the greater actuation force a stiffer, more reliable, return spring 34 may be used. This stiffer spring 34, in turn, results in faster return times compared to prior art springs, which leads to faster cutting speeds.

Figure 2:
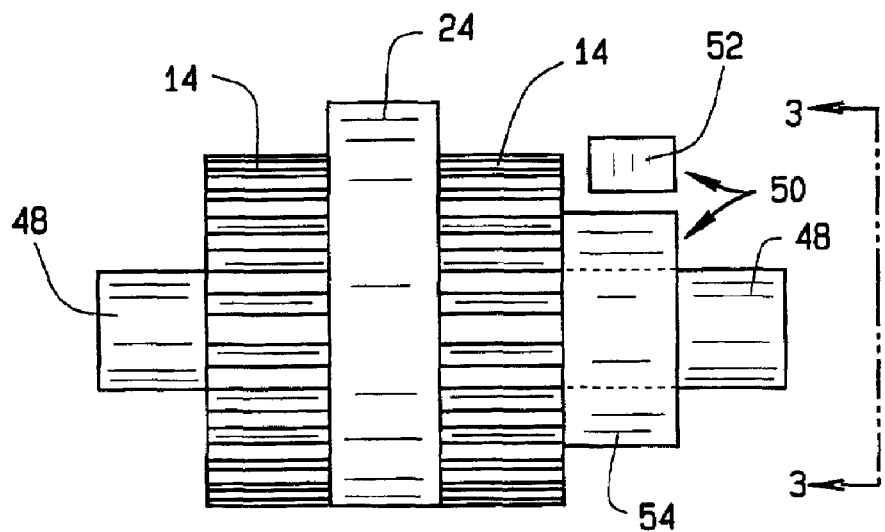
FIG. 2 is a side elevation of a portion of a vitrectomy cutter in accordance with the present invention.
Figure 3:
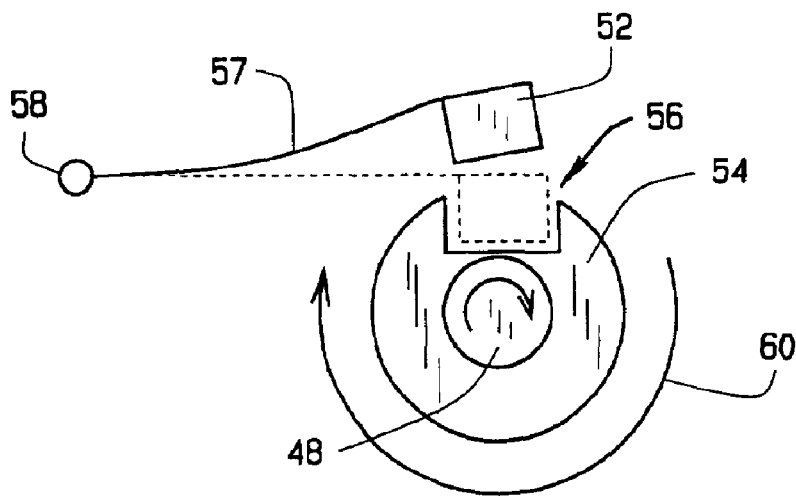
FIG. 3 is a partial front elevation of a brake in accordance with the present invention.

In use, it is often desirable to stop the reciprocation of the vitrectomy probe 38 very quickly and in a pre-determined position. Typically, it is desired to stop the cutter 10 where the probe 38 is in a retracted position. FIGS. 2 and 3 disclose a brake for selectively stopping the rotation of the cam 24. As shown in FIG. 2, the cam 24 and vane 14 assembly rotates about a shaft 48, and includes a brake 50. Brake 50 includes a block 52 and a notched shaft-portion 54.

As best seen in FIG. 3, brake-block 52 is attached to an opposing end of a resilient arm 57 which is fixedly attached to the housing 10 at point 58. Notched shaft-portion 54 is fixed upon an axis of rotation of the cam 24, such that the notch 56 receives the brake-block 52. It should be appreciated that block 52 and notch 56 may be of varying complementary shapes. For example, block 52 and notch 56 may each be somewhat tapered to allow easier insertion and removal of block 52 with respect to notch 56.

Arm 57 is preferably formed of a resilient material, such as plastic, steel, or other suitable material. The resilient arm 57 is sufficiently wide and light-weight enough to be deflected by the pressurized fluid (flowing in the direction of arrow 60) to allow rotation of the cam 24 when the pressurized fluid is flowing in the direction of arrow 60. The combined weight of block 52 and arm 57 must be light enough to be deflected by the flowing pressurized fluid and substantial enough to remain within notch 56 after the fluid flow stops. The resilient arm 57 causes the brake-block 52 to be received within the notch 56 after the pressurized fluid has been cut-off from the inlet 16 (shown by the dashed outline of arm 56 and block 52). In this way, brake 50 is structured to stop rotation of cam 24 in less than one revolution of the cam 24 after the pressurized fluid has been cut-off from the inlet 16. The disclosed brake 50 is but one example of a brake that may be used. Other suitable brakes may also be used.

I claim:

1. A vitreous cutter comprising:
   a housing;
   a plurality of vanes rotatably attached within the housing;
   an inlet for receiving pressurized fluid causing rotation of the vanes;
   an outlet for allowing the pressurized fluid to exit the cutter;
   a cam attached to the vanes and rotatably attached within the housing and structured to rotate upon rotation of the vanes; and
   a vitrectomy probe contained within the housing and structured for reciprocal movement caused by rotating the cam;
   a brake for selectively stopping rotation of the cam;
   wherein the brake is structured to stop rotation of the cam in less than one (1) revolution of the cam after the pressurized fluid has been cut-off from the inlet, such that the probe is stopped in a retracted position.

2. The vitreous cutter of claim 1 wherein the brake further includes:
   a resilient arm fixedly attached to the housing at one end;
   a brake-block attached to an opposing end of the arm;
   a notched shaft-portion fixed upon an axis of rotation of the cam such that the notch receives the brake-block; and
   wherein the resilient arm is deflected by the pressurized fluid to allow rotation of the cam and where the arm causes the brake-block to be received within the notch after the pressurized fluid has been cut-off from the inlet.

* * * * *